US009463437B2

(12) United States Patent
Self et al.

(10) Patent No.: US 9,463,437 B2
(45) Date of Patent: Oct. 11, 2016

(54) METHODS FOR SCAVENGING NITRIC OXIDE USING CERIUM OXIDE NANOPARTICLES

(71) Applicants: William Self, Orlando, FL (US); Sudipta Seal, Orlando, FL (US); Janet Dowding, Orlando, FL (US)

(72) Inventors: William Self, Orlando, FL (US); Sudipta Seal, Orlando, FL (US); Janet Dowding, Orlando, FL (US)

(73) Assignee: University of Central Florida Research Foundation, Inc., Orlando, FL (US)

( * ) Notice: Subject to any disclaimer, the term of this patent is extended or adjusted under 35 U.S.C. 154(b) by 0 days.

(21) Appl. No.: 13/767,482

(22) Filed: Feb. 14, 2013

(65) Prior Publication Data

US 2014/0227368 A1    Aug. 14, 2014

(51) Int. Cl.
*B01J 23/10* (2006.01)
*A61K 33/24* (2006.01)
*C02F 1/70* (2006.01)
*B01D 53/56* (2006.01)
*C02F 1/68* (2006.01)

(52) U.S. Cl.
CPC ............... *B01J 23/10* (2013.01); *A61K 33/24* (2013.01); *B01D 53/565* (2013.01); *C02F 1/70* (2013.01); *B01D 2253/1124* (2013.01); *B01D 2253/304* (2013.01); *B01D 2255/2065* (2013.01); *B01D 2255/9202* (2013.01); *B01D 2257/404* (2013.01); *C02F 1/683* (2013.01); *Y10T 436/177692* (2015.01)

(58) Field of Classification Search
CPC .................. Y10S 977/773; C08K 2003/2213
See application file for complete search history.

(56) References Cited

U.S. PATENT DOCUMENTS

| | | |
|---|---|---|
| 5,089,860 A | 2/1992 | Deppe et al. |
| 5,411,647 A | 5/1995 | Johnson et al. |
| 5,486,359 A | 1/1996 | Caplan et al. |
| 5,910,311 A | 6/1999 | Boussouira |
| 5,961,993 A | 10/1999 | Boussouira |
| 6,042,714 A | 3/2000 | Lin et al. |
| 6,103,247 A | 8/2000 | Boussouira |
| 6,139,985 A | 10/2000 | Borglum et al. |
| 6,316,012 B1 | 11/2001 | N'Guyen |
| 6,327,074 B1 | 12/2001 | Bass et al. |
| 6,368,577 B1 | 4/2002 | Kropf et al. |
| 6,406,685 B1 | 6/2002 | Philippe |
| 6,468,551 B1 | 10/2002 | Diec |
| 6,497,863 B1 | 12/2002 | Wachter |
| 6,497,875 B1 | 12/2002 | Sorrell et al. |

(Continued)

FOREIGN PATENT DOCUMENTS

WO    WO 99/15891       4/1999
WO    WO 03/059263 A2   7/2003

(Continued)

OTHER PUBLICATIONS

JM Dowding, T Dosani, A Kumar, S Seal, WT Self. "Cerium oxide nanoparticles scavenge nitric oxide radical (*NO)." Chem. Commun., vol. 48, 2012, pp. 4896-4898.*

(Continued)

*Primary Examiner* — Isaac Shomer
(74) *Attorney, Agent, or Firm* — Timothy H. Van Dyke; Beusse, Wolter, Sanks & Maire, PLLC

(57) ABSTRACT

The present invention includes a method for scavenging nitric oxide. The method includes contacting the nitric oxide with cerium oxide nanoparticles having a low 3+/4+ ratio.

6 Claims, 5 Drawing Sheets

(56) References Cited

U.S. PATENT DOCUMENTS

| | | | |
|---|---|---|---|
| 6,501,590 B2 | 12/2002 | Bass et al. | |
| 6,592,746 B1 | 7/2003 | Schmid-Schoenbein et al. | |
| 6,654,161 B2 | 11/2003 | Bass et al. | |
| 6,844,387 B2 | 1/2005 | Bass et al. | |
| 6,890,896 B1 | 5/2005 | Shashoua | |
| 7,005,504 B2 | 2/2006 | Hsei et al. | |
| 7,075,707 B1 | 7/2006 | Rapaport et al. | |
| 7,141,227 B2 | 11/2006 | Chan | |
| 7,270,813 B2 | 9/2007 | Shimp et al. | |
| 7,347,987 B2 | 3/2008 | McGinnis et al. | |
| 7,419,516 B1* | 9/2008 | Seal | B82Y 30/00 44/301 |
| 7,431,758 B2 | 10/2008 | Ota et al. | |
| 7,442,686 B2 | 10/2008 | Lasko et al. | |
| 7,471,706 B2 | 12/2008 | Bass et al. | |
| 7,504,356 B1 | 3/2009 | Self et al. | |
| 7,507,480 B2 | 3/2009 | Sugama | |
| 7,534,453 B1 | 5/2009 | Rzigalinski et al. | |
| 7,563,459 B2 | 7/2009 | Phillips et al. | |
| 7,642,250 B2 | 1/2010 | Williams | |
| 7,687,505 B2 | 3/2010 | Sugaya | |
| 7,725,802 B2 | 5/2010 | Katusic et al. | |
| 7,772,375 B2 | 8/2010 | Greferath et al. | |
| 7,888,119 B2 | 2/2011 | Sugaya et al. | |
| 7,899,093 B1 | 3/2011 | Bass et al. | |
| 7,906,147 B2 | 3/2011 | Hainfeld et al. | |
| 7,924,617 B2 | 4/2011 | Yip | |
| 8,080,420 B2 | 12/2011 | Sugaya | |
| 8,097,270 B2 | 1/2012 | Ketelson et al. | |
| 8,172,901 B2 | 5/2012 | Altman et al. | |
| 2003/0050709 A1 | 3/2003 | Noth et al. | |
| 2003/0187077 A1 | 10/2003 | Chane-Ching | |
| 2003/0228277 A1 | 12/2003 | Gehlsen | |
| 2004/0062753 A1 | 4/2004 | Rezania et al. | |
| 2004/0110633 A1* | 6/2004 | Deevi et al. | 502/304 |
| 2005/0159820 A1 | 7/2005 | Yoshikawa et al. | |
| 2005/0164377 A1 | 7/2005 | Miyabayashi et al. | |
| 2005/0171192 A1 | 8/2005 | Gehlsen | |
| 2006/0110440 A1 | 5/2006 | Sugaya | |
| 2006/0280729 A1 | 12/2006 | Mistry | |
| 2007/0003621 A1 | 1/2007 | Nangia et al. | |
| 2007/0072825 A1 | 3/2007 | Williams | |
| 2008/0142707 A1* | 6/2008 | Barnard | G01N 23/223 250/305 |
| 2009/0042751 A1* | 2/2009 | Narayan | 508/155 |
| 2009/0087493 A1 | 4/2009 | Dai et al. | |
| 2009/0098574 A1 | 4/2009 | Brisson et al. | |
| 2010/0088949 A1* | 4/2010 | Reed | B82Y 30/00 44/322 |
| 2010/0151000 A1 | 6/2010 | Thomas et al. | |

FOREIGN PATENT DOCUMENTS

| | | |
|---|---|---|
| WO | WO 2006/118954 A2 | 11/2006 |
| WO | WO 2007/002662 A2 | 1/2007 |
| WO | WO 2008/064357 A2 | 5/2008 |
| WO | WO 2009/132277 A1 | 10/2009 |

OTHER PUBLICATIONS

Electronic Supplemental Information for JM Dowding, T Dosani, A Kumar, S Seal, WT Self. "Cerium oxide nanoparticles scavenge nitric oxide radical (*NO)." Chem. Commun., vol. 48, 2012. There are 8 pages of supplemental information, which are not numbered.*

T Masui, T Ozaki, KI Machida, GY Adachi. "Preparation of ceria-zirconia sub-catalysts for automotive exhaust cleaning." Jounral of Alloys and Compounds, vol. 303-304, 2000, pp. 49-55.*

NJ Lawrence. "Synthesis and Catalytic Activity of Nanostructured Cerium Oxide." Masters Thesis, University of Nebraska, Dec. 1, 2010. Pages: four initial unnumbered pages, p. i-vi and pp. 1-89 (99 total sheets).*

C Xu, X Qu. "Cerium oxide nanoparticle: a remarkably versatile rare earth nanomaterial for biological applications." Nature Publishing Group Asia Materials, vol. 6 e90, 2014, pp. 1-16.*

Sokolov, et al. ,"Real-time vital optical imaging of precancer using anti-epidermal growth factor receptor antibodies conjugated to gold nanoparticles." Cancer Res. 2003, vol. 63:1999, 2004.

Niu, J., et al. "Cardiovascular effects of cerium oxide nanoparticles in a transgenic murine model of cardiomyopathy," Cardiovas. Res. Nov. 30, 2006, Nov. 2006, vol. 73, No. 3, pp. 549-559.

Qureshi, M.A., et al. "Increased exhaled nitric oxide following autologous peripheral hemotopietic stem cell transplantation; a potential marker of idopathic pneumonia syndrome," Chest, Jan. 2004, vol. 125, No. 1, pp. 281-287.

Ohgushi, et al., "Stem Cell Technology and Bioceramics: From Cell to Gene Engineering", J. Biomed. Mat. Res. 48: 913-927; 1999.

Dal Maschio, et al., "Influence of Ce3+/Ce 4+ ratio on phase stability and residual stress field in ceria-yttria stabilized zirconia plasma-sprayed coatings", J. Mat. Sci. 27: 5591-5596; 1992.

Ramsfjell, et al., "Distinct Requirements for Optimal Growth and in Vitro Expansion of Human CD341CD382 Bone Marrow Long-Term Culture-Initiating Cells (LTC-IC), Extended LTC-IC, and Murine in Vivo Long-Term Reconstituting Stem Cells", Blood 99: 4093-4102; 1999.

Devasenpathi, et al., "Forming near net shape free-standing components by plasma spraying", Mat. Let. 57: 882-886; 2002.

Imamura, et al. "Drusen, choridal neovascularization and retinal pigment epithelium dysfunction in SOD1-deficient mice: A model of age-related macular degeneration," PNAS, vol. 103, No. 30; 11282-11287 (Jul. 25, 2006).

Hollyfield, et al. "Oxidative damage-induced inflammation initiates age-related macular degeneration," Nature Medicine, vol. 14, pp. 194-198 (2008).

Birch, et al. Age-related macular degeneration: a target for nano-technology derived medicines. International Journal of Nanomedicine, 2007, 2(1), 65-77.

Maulik, N. Reactive oxygen species drives myocardial angiogenesis? Antioxidants & Redox Signaling, 2006, 8 (11-12) 2161-2168.

Kuchibhatla et al., "Hierarchical assembly of inorganic nanostructure building blocks to octahedral superstructures a true template-free self-assembly", Nanotechnology, 2007, vol. 18, pp. 1-4.

Ohia, et al. "Pharmacological consequences of oxidative stress in ocular tissues," Mutation Research, 2005, 579, 22-36.

Liu, et al. "Subtype lesions of neovascular age-related macular degeneration in Chinese paitents," Braefe's Arch Clin Exp Opthalmol, 2007, 245, 1441-1445.

Silva. "Seeing the benefits of ceria," Nature Nanotechnology, 2006, 1, 92-94.

Hahn, et al. "Maculas affected by Age-Related Macular Degeneration Contain Increased Chelatable Iron in the Retinal Pigment Epithelium and Bruch's Membrane,"Arch. Opthalmol. 2003, 121, 1099-1105.

Haywood, et al. "Inflammation and Angiogenesis in Osteoarthritis," Arthritis & Rheumatism, 2003, 48 (8), 2173-2177.

Chen, et al. Rare Earth Nanoparticles Prevent Retinal Degeneration Induced by Intracellular Peroxides: Nature Nano Technology, 1(2) 142-148 (2006).

Moongkarndi, et al. "Antiproliferation, antioxidation and induction of apoptosis by *Garcinia mangostana* (mangosteen) on SKBR3 human breast cancer cell line," J. of Ethno-Pharmacology, vol. 90, (2004) pp. 161-166.

Margrain, et al. "Do blue light filters confer protection against age-related macular degeneration?", Progress in Retinal and Eye Research, vol. 23 (2004) pp. 523-531.

Bailey, et al. "Cerium Oxide Nanoparticles Extend Cell Longevity and Act as Free Radical Scavengers," online (retrieved on Apr. 24, 2006) from: http://www.med.miami.edu/mnbws/Rzigalinski11.html.

Tsai, Ming-Shyong. "The Study of the synthesis of nano-grade cerium oxide powder," Materials Letters 58, 2270-2274 (2004).

Rzigalinski, Beverly Ann, et al. "Cerium Oxide nanoparticles increase the lifespan of cultured brain cells and protect against free

(56) References Cited

OTHER PUBLICATIONS radical mechanical trauma" FASEB Journal, vol. 17 No. 4-5, p. Abstract No. 377.24 URL, XP008095016 & FASEB Meeting on Experimental Biology: Translating the Genome, San Diego, CA, USA, Apr. 11-15, 2003 ISSN: 0892-6638 *Abstract*.
Cook, et al. "Neuronal Damage induced by polychlorinated biphenyls is partically reversed by cerium oxide nanoparticles" [online] vol. 2003, 2003, XP008095032 Retrieved from the internet: URL http://sfn.scholarone.com/itin2003/main.htm]?new_page_id=126 &abstract_id=14513&p_num=669.13&is_tech=0> [retrieved on Aug. 5, 2008] *abstract*.
Tusnekawa, S., et al. "Lattice relaxation of monosize Ce02-x nanocrystalline particles" Applied Surface Science Elsevier Netherlands, vol. 152, No. 1-2, Nov. 1999, pp. 53-56.
Hooper, Claire, Y., et al. "New treatment in age-related macular degeneration" Clinical & Experimental Opthalmology, Oct. 2003, pp. 376-391.
Qi, et al. "Redispersible Hybrid Nanopowders; Cerium Oxide Nanoparticle complexes with Phosphonated-PEG Oligomers," ACS Nano, 2008, vol. 2(5), pp. 879-888.
Otsuka, et al. "PEGylated nanoparticles for biological and pharmaceutical applications," Advanced Drug Delivery Reviews, 2003, vol. 55, pp. 403-419.
Olivier, et al. "Synthesis of pegylated immunonanoparticles." Pharmaceutical Research, Aug. 2002, vol. 19, No. 8, pp. 1137-1143.
Shui, Y.B., et al. "Morphological observation on cell death an dphagocytosis induced by ultraviolet irradiation in a cultured human lens epithelial cell line," Dec. 2000, vol. 71, pp. 609-618.
Xijuan, et al. "Size-dependent optical properties of nanocrystalline Ce02:Er obtained by combustion synthesis," Sep. 24, 2001, Phys. Chem. Chem Phys., vol. 3, pp. 5266-5269.
Guo, "Green and red upconversion luminescence in Ce02:Er3+ powders produced by 785 nm laser," Jounral of Solid State Chemistry 180, p. 127-131, 2007.
Perez, J. M., et al. "Synthesis of Biocompatible Dextran-Coated Nanoceria with pH-Dependent Antioxidant Properties," Small, vol. 4 No. 5, 2008, pp. 552-556.
Pirmohamed, et al. "Nanoceria exhibit redox state-dependent catalase mimetic activity," Chem. Comm, 2010, 46, pp. 2736-2738.
Nazem, et al. "Nanotechnology for Alzheimer's disease detection and treatment." Insciences J., 2011, vol. 1(4), pp. 169-193.
Karakoti, et al. "Direct Synthesis of Nanoceria in Aqueous Polyhydroxyl Solutions." J. Phys. Chem. C, vol. 111, No. 46, 2007, pp. 17232-17240.
Tarnuzzer, et al. "Vacancy Engineered Ceria Nanostructures for Protection from Radiation-Induced Cellular Damage," Nano Lett, vol. 4, No. 12, pp. 2573-2577.
Heckert, et al. "The role of cerium redox state in the SOD mimetic activity of nanoceria," Biomaterials, 29, 2008, pp. 2705-2709.
Schubert, et al. "Cerium and yttrium oxide nanoparticles are neuroprotective," Feb. 2006, Biochemical and Biophysical Research Communications, 342, p. 86-91.
Zhang, et al. Cerium oxide nanoparticles: size selective formation and structure analysis, Jan. 2002, Applied Physics Letters, vol. 81, No. 1, p. 127-129.
Patil, et al. "Surface-derived nanoceria with human carbonic anhydrase Ii inhibitors and flourphores: a potential drug delivery device." J. Phys. Chem. C., 2007, vol. 111, No. 24, pp. 8437-8442.
Patil, et al. "Synthesis of nanocrystalline ceria particles for high temperature oxidation resistant coating," Journal of Nanoparticle Research, 2002, vol. 4: ppl. 433-438.
Jin, et al. "Nanopartical-mediated drug delivery and gene therapy," Biotechnol. Prog, 2007, vol. 23, pp. 32-41.
Eck, et al. "PEGylated gold nanoparticles conjugated to monoclonal F19 antibodies as targeted labeling agents for human pancreatic carcinoma tissue," ACS Nano, 2008, vol. 2(11) pp. 2263-2272.
Nafee. Dissertation entitled "Cationically-modified nanoparticles for the polmonary delivery of the telomerase inhibitor 2'-O-Methyl RNA for the treatment of lung cancer," Dissertation zur Erlangung des Grades des Doktors der, Naturwissenschaftern der Naturwissenschaftilch-Technischen Fakul't III Chemie, Pharmazie, Bio-und Werstoffwissenschaften der Universit des Saarlandes, 2008.
Suh et al., "Multifunctional nanosystems at the interface of physical and life sciences", Nano Today, 2009, vol. 4, pp. 27-36.
Suzuki et al., "Preparation and characteristics of magnetite labelled antibody with the use of poly(ethylene glycol) derivatives", Biotechnol. Appl. Biochem., 1995, vol. 21, pp. 335-345.
Monte et al., "Inhibition of lymphocyte induced angiogenesis by free radical scavengers", Free Radic Biol Med, 1994, vol. 17, pp. 259-266.
Buettner, et al., "Ascorbate (vitamin C, It's Antioxidant Chemist", Presentation.
PCT/US2011/0044329; PCT International Search Report and Written Opinion.
A. B. Knott et al., "Nitric Oxide in Health and Disease of the Nervous System", Antioxid. Redox Signaling, 2009, vol. 11, pp. 541-554.
E. Isenovic et al., "Regulation of Endothelial Nitric Oxide Synthase in Pathophysiological Conditions", Cardiovasc. Hematol. Disord. Drug Targets, 2011, vol. 11, pp. 669-702.
M. C.Martinez et al. "Reactive Nitrogen Species: Molecular Mechanisms and Potential Significance in Health and Disease", Antioxid. Redox Signaling, 2009, vol. 11, pp. 669-702.
D. Pietraforte et al., "Peroxynitrite-dependent modifications of tyrosine residues in hemoglobin. Formation of tyrosyl radical(s) and 3-nitrotyrosine", Amino Acids, 2003, vol. 25, pp. 341-350.
T. Masui et al., "Preparation of ceria-zirconia sub-catalysts for automotive exhaust cleaning", J. Alloys Compd., 2000, vol. 303-304, pp. 49-55.
Y. Y. Tsai et al., "Reactive oxygen species scavenging properties of $ZrO_2-CeO_2$ solid solution nanoparticles", Nanomedicine, 2008, vol. 3, pp. 637-645.
R. M. Ferrizz et al., "Reaction of NO on $CeO_2$ and $Rh/CeO_2$ thin films supported on $a-Al_2O_3(0001)$ and YSZ(100)", Surf. Sci., 2001, vol. 476, pp. 9-21.
M. Niwa et al., "Absorption of Nitric Oxide on Cerium Oxide", J. Colloid Interface Sci., 1982, vol. 86, pp. 260-265.
G. S. Qi et al, "$MnO_x-CeO_2$ mixed oxides prepared by coprecipitation for selective catalytic reduction of NO with $NH_3$ at low temperatures", Appl. Catal., B, 2004, vol. 51, pp. 93-106.
A. Martinez-Arias et al., :NO Reaction at Surface Oxygen Vacancies generated in Cerium Oxide, J. Chem. Soc., Faraday Trans., 1995, vol. 91, pp. 1679.
M. A. Sharpe et al., "Oxidation of nitric oxide by oxomanganese—salen complexes: a new mechanism for cellular protection by superoxide dismutase/catalase mimetics", Biochem. J., 2002, vol. 366, pp. 97-107.
M. E. Murphy et al., "Nitric Oxide Assay Using Hemoglobin Method",Methods Enzymol., 1994, vol. 233, pp. 240-250.
M. H. Lim et al., "Visualization of nitric oxide in living cells by a copper-based fluorescent probe", Nat. Chem. Biol., 2006, vol. 2, pp. 375-380.
S. Singh et al., "A phosphate-dependent shift in redox state of cerium oxide nanoparticles and its effects on catalytic properties", Biomaterials, 2011, vol. 32, pp. 6745-6753.
B. B. Wayland et al., "Spectroscopic Studies and Bonding Model for Nitric Oxide Complexes of Iron Porphyrins", J. Am. Chem. Soc., 1974, vol. 96, pp. 6037-6041.
M. R. Filipovic et al., "NO Dismutase Activity of Seven-Coordinate Manganese(II) Pentaazamacrocyclic Complexes", Angew. Chem., Int. Ed., 2008, vol. 47, pp. 8735-8739.
A. Y. Estevez et al., "Neuroprotective mechanisms of cerium oxide nanoparticles in a mouse hippocampal brain slice model of ischemia", Free Radical Biol. Med., 2011, vol. 51, pp. 1155-1163.
M.H. Lim et al., "Direct nitric oxide detection in aqueous solution by copper(II) fluorescein complexes", 2006, J Am Chem Soc vol. 128, pp. 14364-14373.
MJ Kampschreur et al, "Unraveling the source of nitric oxide emission during nitrification", 2007, Water Environ Res., vol. 79(13), pp. 2499-2509.

(56) References Cited

OTHER PUBLICATIONS

M. A. Ebrahimazadeh et al., "Nitric oxide radical scavenging potential of some Elburz medicinal plants", 2010, African J of Biotechnol., vol. 9(32), pp. 5212-5217.

G. Aliev et al., "Nitric Oxide as an initiator of brain lesions during the development of Alzheimer disease", 2009, Neurotox. Res., vol. 16, pp. 293-305.

L. Zhang et al., "Role of nitric oxide in Parkinson's disease", 2006, Pharmacol. Ther, vol. 109, pp. 33-41.

A.K. Nath et al, "The roles of nitric oxide in murine cardiovascular development", 2006, Dev. Biol, vol. 292, pp. 25-33.

F. Parkinson et al., "The role of nitric oxide in multiple sclerosis", Mar. 1997, J Mol Med (Berl), vol. 75(3), pp. 174-186.

J. Dowling et al., "Cerium oxide nanoparticles scavenge nitric oxide radical (•NO)", 2012, Chem. Commun, vol. 48, pp. 4896-4898.

F.J. Bonte et al., "Tc-99m HMPAO SPECT in the differential diagnosis of the dementias with histopathologic confirmation", Jul. 2006, Clin Nucl Med, vol. 31 (7), pp. 376-378.

N.J. Dougall et al, "Systematic review of the diagnostic accuracy of 99mTc-HMPAO-SPECT in dementia", 2004, Am J . Genatr Psychiatry, vol. 12 (6), pp. 554-570.

G. De Meyer et al., "Diagnosis-Independent Alzheimer Disease Biomarker Signature in Cognitively Normal Elderly People", Aug. 2010, Arch Neurol, vol. 67 (8), pp. 949-956.

A.S., Karakoti et al., ",Nanoceria as antioxidant: Synthesis and biomedical applications", 2008, JOM vol. 60, pp. 33-37.

R. Stuven et al, "Nitrification and Denitrification as a Source for NO and NO2 Production in High Strength Wastewater", 2001, Wat. Res. vol. 35, No. 8, pp. 1905-1914.

Dong et al., "Activation of glassy carbon electrodes by dispersed metal oxide particles", J. Electrochem Soc., 1984, pp. 813-819.

\* cited by examiner

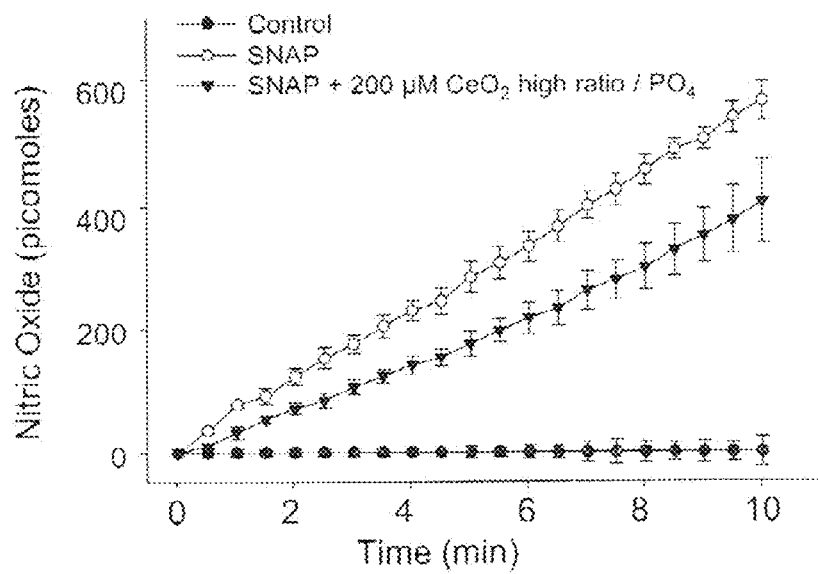
FIG. 5
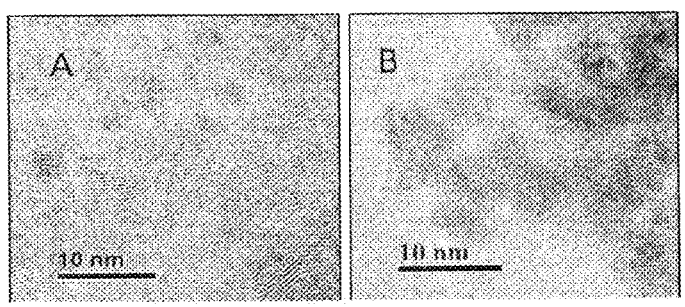
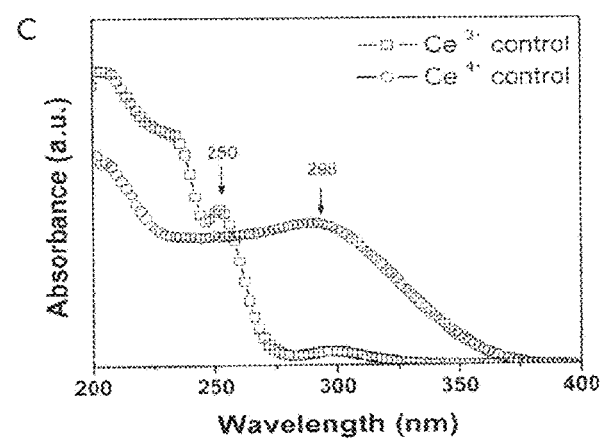
FIGS. 6A-C

METHODS FOR SCAVENGING NITRIC OXIDE USING CERIUM OXIDE NANOPARTICLES

STATEMENT OF GOVERNMENT RIGHTS

This invention was made with Government support under agency contract/grant no. R01AG031529 awarded by the National Institutes of Health and under CBET0708172 awarded by the National Science Foundation. The Government has certain rights in this invention.

FIELD OF THE INVENTION

The present invention relates to cerium oxide nanoparticles, and more particularly to devices and compositions comprising cerium oxide nanoparticles having a lower 3+/4+ ratio for scavenging nitric oxide molecules, and to methods for their use.

BACKGROUND OF THE INVENTION

As known by those having ordinary skill in the art, chemically, most of the rare earth (RE) elements (atomic numbers 57 through 71) are trivalent. Cerium alone is known to form compounds with a valence of +4, such as $CeO_2$ (ceria). Cerium is believed to be a unique material with regard to the mixed valence states provided, both +3 and +4. Cerium of valence +3 is generally referred to as cerous, while with valence +4 is generally referred to as ceric. Cerium oxide includes both ceric oxide and cerous oxide. Cerous oxide is also known as Cerium III oxide and has the formula $Ce_2O_3$. Ceric oxide is known as ceria, cerium dioxide and cerium IV oxide and has the chemical formula $CeO_2$.

Cerium oxide has been used as a catalyst in industrial applications because of its potent redox-active properties, including as a catalyst, to remove carbon monoxide, hydrocarbons and nitric oxide species ($NO_x$) from exhaust gas.[5,6] Nitric oxide is formed, for example, when the nitrogen present in atmospheric air is subjected to high temperatures, such as those normally found in conventional combustion and incineration processes. In addition, nitric oxide is well-known to be formed during wastewater treatment, such as with the use of bacteria, such as *Nitrosomonas*, which are widely used to eliminate nitrogenous compounds from wastewater. A number of other processes produce nitric oxide at measurable levels, such as certain etching and welding processes. Nitric oxide is rapidly oxidized in air to nitrogen dioxide, which is a major pollutant; therefore, improved methods for its removal and detection are desired.

BRIEF DESCRIPTION OF THE DRAWINGS

FIG. 5 shows the effective scavenging of •NO by $CeO_2$ NPs with high level of surface oxygen vacancies upon incubation with phosphate. Concentration of •NO in the presence or absence of $CeO_2$ NPs was quantified as described in Supplementary FIG. 6. Closed circles=25 mg/mL Hb alone; open circles=25 mg/mL Hb+200 µM SNAP; closed triangles=25 mg/mL Hb+200 µM SNAP +200 µM $CeO_2$ high $Ce^{3+}$/$PO_4$. Graph is representative of 3 or more experiments.

FIGS. 6A-C are a comparison of $CeO_2$ NPs 3+ and 4+. A: HR-TEM image of $CeO_2$ NP higher 3+ B: HR-TEM image $CeO_2$ NPs higher 4+ C: UV-vis spectroscopy.

DETAILED DESCRIPTION OF THE INVENTION

Figure 1:
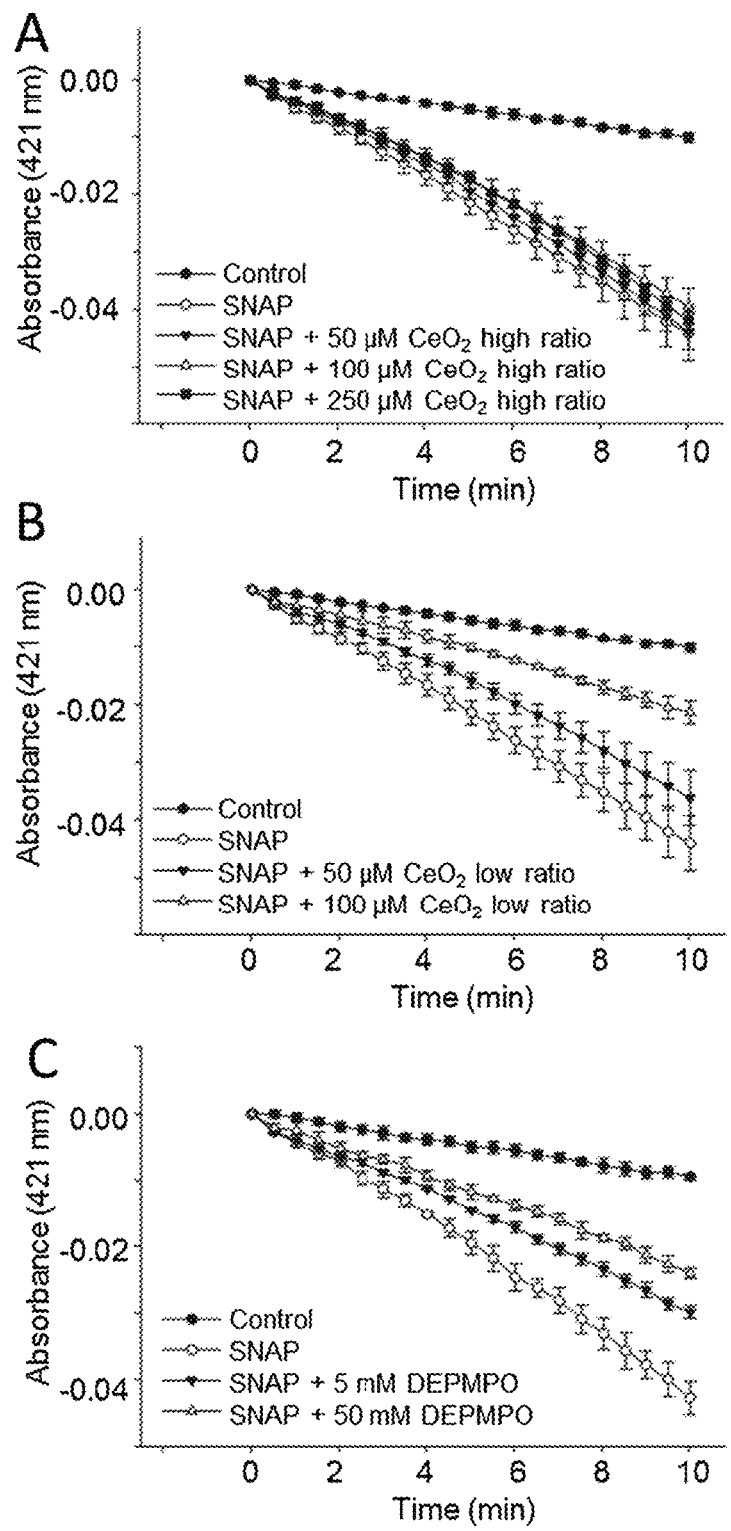
FIG. 1A-1C show that cerium oxide nanoparticles ($CeO_2$ NPs) with low 3+/4+ ratio scavenge •NO. Represented in all graphs: closed circles=25 µg/mL Hb alone; open circles=25 µg/mL Hb+200 µM SNAP. (A) $CeO_2$ NPs with high 3+/4+ ratio. (B) $CeO_2$ NPs with low 3+/4+ ratio. (C) DEPMPO addition. $CeO_2$ NPs or DEPMPO were added at the concentrations indicated. Graph is representative of 3 or more experiments.

The present inventors have surprisingly found that the low ratio 3+/4+ cerium oxide nanoparticles ($CeO_2$ NPs) described herein are especially suitable for scavenging nitric oxide radicals. By "low ratio" it is meant the percentage of cerium in the 3+ state is lower than the percentage of cerium in the 4+ state, and therefore a reduced number of oxygen vacancies are present, as determined, for example, by x-ray photoelectron spectroscopy (XPS). These NO scavenging properties are particularly surprising in view of the superoxide scavenging properties of $CeO_2$, which are conversely correlated with an increased level of cerium in the 3+ state ($CeO_2$ NPs with high 3+/4+ ratio, and therefore an increased number of oxygen vacancies).

In accordance with one aspect, there is provided a method for scavenging nitric oxide comprising contacting the nitric oxide with ceria nanoparticles having a low 3+/4+ ratio (also referred to as "low ratio cerium oxide nanoparticles" herein). The method may be suitable for use in industrial environments to scavenge nitric oxide radicals, which may be formed as a result of a process such as combustion, wastewater treatment, etching processes, welding, or the like. In other embodiments, the application may be for the detection of nitric oxide, such as with the detection of nitric oxide from the irradiation of nitrogen-based explosives with a suitable energy source. In still other embodiments, the method may be utilized in vivo for the treatment or prevention of disorders characterized by abnormal nitric oxide production.

In accordance with yet another aspect, there is provided a method for reducing an amount of nitric oxide within a nitric oxide-containing fluid stream comprising contacting the nitric oxide with a plurality of cerium oxide nanoparticles having a low 3+/4+ ratio. In certain embodiments, the nitric oxide-containing stream is a by-product of combustion of a fuel in the presence of air. In other embodiments, the nitric oxide-containing fluid stream may be from a wastewater treatment process.

In accordance with another aspect, there is provided a device for reducing an amount of nitric oxide within a nitric oxide-containing fluid stream. The device comprises a housing and a quantity of cerium oxide nanoparticles having a low 3+/4+ ratio disposed within the housing. An inlet is provided in the housing, which is configured for receiving the nitric-oxide containing fluid stream to be treated with the low ratio cerium oxide nanoparticles. An outlet in the housing is also provided for allowing release of a fluid stream having a reduced amount of nitric oxide relative to the nitric-oxide containing fluid stream after contact with the low ratio cerium oxide nanoparticles.

In accordance with another aspect, there is provided a method for detecting an amount of nitric oxide in a sample. The method comprises contacting the sample with an effective amount of cerium oxide nanoparticles having a low 3+/4+ ratio. Thereafter, the method comprises detecting a change in oxidation state of the cerium oxide nanoparticles, the detection being indicative of the presence of nitric oxide in the sample.

In accordance with yet another aspect, there is provided a method for treating a condition associated with elevated levels of nitric oxide. The method comprises administering an effective amount of cerium oxide nanoparticles having a low 3+/4+ ratio to the subject to reduce an amount of nitric oxide in the subject.

In accordance with still another aspect, there is provided a method for treating a subject with elevated levels of peroxynitrite formed from reaction of nitric oxide and superoxide molecules. The method comprises administering an effective amount of cerium oxide nanoparticles having a low 3+/4+ ratio to the subject to scavenge a quantity of nitric oxide molecules in the subject, thereby preventing production of peroxynitrite in the subject.

In accordance with still another aspect, there is provided a pharmaceutical composition for scavenging nitric oxide in a subject comprising an effective amount of cerium oxide nanoparticles having a low 3+/4+ ratio and a pharmaceutically acceptable carrier.

In accordance with still another aspect, there is provided a method of reducing brain inflammation in a patient comprising administering a therapeutically effective amount of cerium oxide nanoparticles having a low 3+/4+ ratio to the patient. The cerium oxide nanoparticles are effective to reduce nitrite oxide levels in the brain, thereby reducing peroxynitrite levels in the brain.

1.1 Definitions

It is important to an understanding of the present invention to note that all technical and scientific terms used herein, unless defined herein, are intended to have the same meaning as commonly understood by one of ordinary skill in the art. The techniques employed herein are also those that are known to one of ordinary skill in the art, unless stated otherwise. Prior to setting forth the invention in detail and for purposes of more clearly facilitating an understanding the invention as disclosed and claimed herein, the following definitions are provided.

As used herein, the use of the word "a" or "an" when used in conjunction with the term "comprising" in the claims and/or the specification may mean "one," but it is also consistent with the meaning of "one or more," "at least one," and "one or more than one."

As used herein, the terms "about" and "approximately" as used herein refers to values that are ±10% of the stated value.

As used herein, the terms "administering," "administration," or the like includes any route of introducing or delivering to a subject a composition (e.g., pharmaceutical composition or wound dressing) to perform its intended function. The administering or administration can be carried out by any suitable route, including topically, orally, intranasally, parenterally (intravenously, intramuscularly, intraperitoneally, or subcutaneously), rectally, or topically. Administering or administration includes self-administration and the administration by another.

As used herein, the term "cardiovascular disease" refers any abnormal condition characterized by dysfunction of the heart and blood vessels. Cardiovascular disease includes but is not limited to atherosclerosis, cerebrovascular disease, and hypertension.

As used herein, the term "condition" includes any disease, disorder, medical condition or other abnormal physical state, including those associated with, related to or involving nitric oxide directly or indirectly in the transmission, presence, and/or progression of the disorder. Such disorders are said to be "related to," "associated with," or mediated (at least in part) by nitric oxide activity.

As used herein, by the term "effective amount" "amount effective," or the like, it is meant an amount effective at dosages and for periods of time necessary to achieve the desired result.

As used herein, the term "fluid" refers to a continuous, amorphous material whose molecules move freely past one another. The fluid typically assumes the shape of its container as is the case when the fluid is a gas, liquefied gas, liquid, or liquid under pressure. In one embodiment, the fluid is a gaseous nitric oxide containing stream. In another embodiment, the fluid is a liquid nitric oxide-containing stream.

As used herein, the term "inflammatory disease" refers to any condition with presentation of inflammatory symptoms, including infectious diseases, allergy diseases, and autoimmune diseases, for example. In one embodiment, the inflammatory disease is an inflammatory autoimmune disease.

As used herein, the term "muscular disease" refers to any condition in which muscle fibers do not function properly, thereby resulting in muscular weakness or decreased muscular function.

As used herein, "neurodegenerative disease" or the like refers to any disorder characterized by gradually progressive, selective loss of anatomically or physiologically related neuronal systems. Exemplary disorders include Alzheimer's disease (AD), Parkinson's disease (PD), amyotrophic lateral sclerosis (ALS), and Huntington's disease (HD).

As used herein, the terms "pharmaceutically acceptable carrier" or "physiologically acceptable carrier" as used herein refer to one or more formulation materials suitable for accomplishing or enhancing the successful delivery of the pharmaceutical composition prepared and delivered according to aspects of the invention.

As used herein, the term "sepsis" refers to the systemic inflammatory response associated with infection.

As used herein, the term "septic shock" refers to a shock state resulting from an infection in a subject, including a bacterial infection.

As used herein, the term "subject" refers to any animal (e.g., a mammal), including, but not limited to, humans, which may be the recipient of a treatment.

As used herein, the terms "treating" or "treatment" or "alleviation" refers to both therapeutic treatment and prophylactic or preventative measures, wherein the objective is to reduce an amount of nitric oxide relative to an amount of nitric oxide without administering an effective amount of cerium oxide nanoparticles.

1.2 Ceria Nanoparticles

The cerium oxide provided in the compositions and methods described herein comprise a low 3+/4+ cerium oxide ratio. In one embodiment, the low ratio cerium oxide comprises from less than 50% $Ce^{3+}$ molecules versus $Ce^{4+}$ molecules. In a particular embodiment, the surface of the biocompatible material comprises 20% or less $Ce^{3+}$ molecules versus $Ce^{4+}$ molecules.

In accordance with one aspect, the cerium oxide nanoparticles have an average particle size (e.g., diameter) of <20 nm, preferably in the range from 1 to 10 nm, and more preferably from 1 to 5 nm. The inventors have found that an average cerium oxide nanoparticle size in the range <20 nm provides an increased percentage of +3 valence states (relative to the generally more numerous +4 states) on the nanoparticle's surface. The increasing percentage of +3 valence states is believed to increase as the cerium oxide nanoparticle size decreases in this size range. Accordingly, in one embodiment, the ratio of cerium oxide in the 3+ valence state vs. the 4+ valence state may be controlled by maintaining a predetermined size ratio of the synthesized nanoparticles.

Exemplary cerium oxide nanoparticles and methods of synthesis thereof that may be used in the present invention include, but are not limited to, those described in U.S. Pat. No. 7,504,356 and Karakoti A S, Monteiro-Riviere N A, Aggarwal R, Davis J P, Narayan R J, Self W T, McGinnis J, Seal S (2008) Nanoceria as antioxidant: Synthesis and biomedical applications. JOM 60: 33-37[32], the entirety of each of which is expressly incorporated by reference herein.

1.3 Industrial Applications

The low ratio cerium oxide nanoparticles may be utilized in any application where the removal of nitric oxide from a sample, e.g., a fluid stream, is desired. Advantageously, cerium oxide can reduce nitric oxide and take the oxygen to form its ceric oxide state. In one aspect, the methods described herein may include contacting a nitric-oxide containing gas stream with cerium oxide nanoparticles having a low 3+/4+ ratio, wherein the nitric oxide-containing gas stream is an exhaust gas stream from a combustion process. Nitric oxide is produced a by-product of combustion of a fuel-air mixture or of fuel in air, and thus may be found in the exhaust gas from automobile or turbine engines. The fuel may be any fuel, such as a hydrocarbon source or natural gas source. Nitric oxide also rapidly oxidizes in air, especially at higher temperatures, to form nitrogen (nitrous) dioxide ($NO_2$), which is a brown toxic gas and a major air pollutant. The cerium oxide nanoparticles will scavenge the nitric oxide molecules before they oxidize into nitrous dioxide. In addition, it is contemplated that cerium oxide may convert harmful carbon monoxide to the less harmful carbon dioxide.

In accordance with another aspect, the methods described herein may include contacting a nitric-oxide containing gas stream with cerium oxide nanoparticles having a low 3+/4+ ratio, wherein the nitric oxide-containing gas stream is a stream from a wastewater treatment process. Wastewater is routinely treated with suitable processes to remove soluble organic matter, suspended solids, pathogenic organisms, and chemical contaminants. In many processes, wastewaster undergoes a nitrification process where ammonia or organic nitrogen is converted to nitrites and nitrates. Thereafter, the wastewater undergoes denitrification, wherein nitrates and/or nitrites are further reduced to nitrogen gas. In either case, the nitrification or denitrication processes may involve the intermediate production of nitric oxide (NO). In the nitrification process, for example, ammonia-oxidizing bacteria may be responsible for NO generation.[33, 34]

In accordance with another aspect, the nitric oxide-containing gas stream may be any other nitric-oxide containing gas stream. Without limitation, the nitric oxide-containing stream may be one produced by contact of nitric acid with organic material such as wood, sawdust, or waste; heating of nitric acid; burning of nitro compounds, contacting of nitric acid on metals, such as in metal etching and pickling. In addition, the nitric oxide-containing stream may be produced by high temperature welding process using an oxyacetylene or electric torch, for example, wherein the nitrogen and oxygen in the air combine to form oxides of nitrogen, such as nitric oxide.

1.4 Detection of Nitric Oxide

The methods for removing nitric oxide form a nitric oxide-containing fluid stream may further comprise a detecting step such that particles may be used as a detector of nitric oxide in a sample. Thus, in accordance with another aspect, there is provided a method for detecting an amount of nitric oxide in a sample. The method comprises contacting the sample with an effective amount of low ratio cerium oxide nanoparticles. Thereafter, the method comprises detecting a change in oxidation state of the cerium oxide nanoparticles, the detection being indicative of the presence of nitric oxide in the sample.

Suitable methods and instrumentation for detecting the change in oxidation state of the low ratio cerium oxide nanoparticles are well-known in the art. Exemplary methods include but are not limited to the use of electrodes, chemiluminescence, and fluorescence as are known in the art, and corresponding instrumentation. In another embodiment, XPS, x-ray photoelectron spectroscopy (Surface Science 563 (2004) 74-82) is used. Exemplary electrochemical sensors within which the low ratio cerium oxide nanoparticles may be incorporated as are described in U.S. Published Patent Application No. 20090071848, the entirety of which is hereby incorporated by reference herein.

The cerium oxide nanoparticles may be utilized for the sensing or detection of nitric oxide from any suitable sample. Without limitation, in one embodiment, the cerium oxide nanoparticles may be utilized in the detection of nitrogen-based explosive materials, such as trinitrotoluene (TNT), cyclotrimethylenetrinitramine (RDX), pentrite (PETN), and ammonium nitrate/fuel oil (e.g., ANFO). As set forth in U.S. Published Patent Application No. 20120145925, nitric oxide (NO) is a characteristic photofragment of nitro-based explosive materials when the explosive material is irradiated with ultraviolet (UV) light. Thus, nitro-based explosives may be irradiated with UV light or another energy source, the resulting ambient air sample may be collected by suitable methods, and contacted with the low ratio cerium oxide nanoparticles. Thereafter, the change in oxidation state of the cerium oxide nanoparticles may be detected.

1.5 Configurations

The low ratio cerium oxide nanoparticles may be disposed in any suitable form or configuration for use in the methods described herein. In one embodiment, the low ratio cerium oxide nanoparticles may be disposed within a device comprising a housing sized and suitable for the associated application. Typically, the housing is formed from an inert material so as to not interfere with the removal of nitric oxide from a nitric oxide-containing stream flowing through the housing. Within the housing, the low ratio cerium oxide nanoparticles may optionally be combined with catalysts, supports, binders, carriers, promoters or other materials suitable for the application as would be appreciated by one skilled in the art. Typically, the housing will have an inlet for receiving a nitric-oxide containing fluid stream to be treated with the low ratio cerium oxide nanoparticles. An outlet in the housing is also provided for allowing release of a fluid stream having a reduced amount of nitric oxide relative to the nitric-oxide containing fluid stream after contact with the low ratio cerium oxide nanoparticles to the environment or to a next process step.

When utilized to treat exhaust gas from combustion, the cerium oxide nanoparticles may be disposed in a geometric form that allows for high NOx reduction efficiency along with a minimal pressure drop. A monolithic form and the use of a monolith as a catalyst carrier are well known to one skilled in the art. A monolith consists of a series of straight, non-interconnecting channels. Onto the walls of the monolith are coated a thin layer of a catalyst-containing material, termed "washcoat" by the trade. It is within the pores of the washcoat that the cerium oxide nanoparticles, and any catalyst(s), binders, and promoters that may be added are located. The catalyst may be any suitable catalyst for reducing NOx, including nitric oxide, such as a platinum group metal. Exemplary systems into which the cerium oxide nanoparticles may be incorporated are set forth in U.S. Pat. Nos. 5,399,324, 5,532,198, and 7,744,840, the entirety of which are each incorporated by reference herein.

1.6 Pharmaceutical Applications

The compositions and methods described herein may also be utilized in the treatment or prevention of any condition associated with elevated levels of nitric oxide. Nitric oxide is now believed to be associated with a variety of physiological processes since being identified as a novel signal molecule. For one, nitric oxide transmits signals from vascular endothelial cells to vascular smooth muscle cells and causes vascular dilation. In addition, nitric oxide also is associated with other vital physiological functions in the respiratory, immune, neuromuscular systems. In the nervous system, NO works as an atypical neural modulator that is involved in neurotransmitter release, neuronal excitability, learning and memory. Besides its role in physiologic processes, nitric oxide also participates in pathogenic pathways underlying a large group of disorders including muscle diseases, such as muscular dystrophy or inflammatory muscle disease; inflammatory bowel disease; sepsis and septic shock; primary headaches, cardiovascular-related conditions, such as reperfusion injury, atherosclerosis, cerebrovascular disease, hypertension, and stroke.[23] Additionally, increasing evidence shows that nitric oxide modulates neurotoxin induced cell damage and is involved in neuronal cell death in Parkinson's disease (PD) and other neurodegenerative disorders, such as Alzheimer's disease, Parkinson's disease, Amyotrophic lateral sclerosis, Friedreich's ataxia, Huntington's disease, or Lewy body disease.[24-26]

Elevated nitric oxide synthesis has been associated with nonspecific immune-mediated cellular cytotoxicity and the pathogenesis of chronic, inflammatory diseases, such as inflammatory autoimmune diseases including rheumatoid arthritis, insulin-dependent diabetes, inflammatory bowel disease, and multiple sclerosis.[27] The role of nitric oxide may be directly related to the disease or indirectly related by its involvement in a pathway, such as by the formation of peroxynitrite by interaction of nitric oxide with the superoxide radical.[28]

Thus, in accordance with one aspect, the compositions described herein may be administered to a subject having or identified as being at risk of developing a muscular disease, inflammatory bowel disease; sepsis; septic shock; primary headaches, an inflammatory disease, a cardiovascular-related condition; and/or a neurodegenerative disorder.

Identification of the individual having or being at risk of developing one or more of the above disorders may be performed by any suitable methods known in the art. For example, a subject at risk of developing a neurodegenerative disease can be identified by detecting or observing a number of different signs and symptoms in the subject. Some of those signs and symptoms include amyloid plaques in the brain, and/or neurofibrillary tangles (NFTs) in the brain.

In the case of Alzheimer's disease, eight cognitive domains are most commonly impaired, including memory, language, perceptual skills, attention, constructive abilities, orientation, problem solving and functional abilities (American Psychiatric Association (2000). Diagnostic and statistical manual of mental disorders: DSM-IV-TR (4th Edition Text Revision ed.). Washington, D.C.: American Psychiatric Association).

Also, a decrease in activity in the temporal lobe is observed in AD development, such as through the use of known imaging techniques such as PET scan or MRI. Thus, according to one embodiment, a patient at risk would be an individual who has impairment in cognition and/or decreased activity in the temporal lobe. When available as a diagnostic tool, single photon emission computed tomography (SPECT) and positron emission tomography (PET) neuroimaging are used to confirm a diagnosis of Alzheimer's in conjunction with evaluations involving mental status examination.[29] In a person already having dementia, SPECT appears to be superior in differentiating Alzheimer's disease from other possible causes, compared with the usual attempts employing mental testing and medical history analysis.[30] Advances have led to the proposal of new diagnostic criteria.

A new technique known as PiB PET has been developed for directly and clearly imaging beta-amyloid deposits in vivo using a tracer that binds selectively to the A-beta deposits. The PiB-PET compound uses carbon-11 PET scanning. Recent studies suggest that PiB-PET is 86% accurate in predicting which people with mild cognitive impairment will develop Alzheimer's disease within two years, and 92% accurate in ruling out the likelihood of developing Alzheimer's. A similar PET scanning radiopharmaceutical compound called (E)-4-(2-(6-(2-(2-(2-([$^{18}$F]-fluoroethoxy)ethoxy)ethoxy)pyridin-3-yl)vinyl)-N-methyl benzenamine, or $^{18}$F AV-45, or florbetapir-fluorine-18, or simply florbetapir, contains the longer-lasting radionuclide fluorine-18, has recently been created, and tested as a possible diagnostic tool in Alzheimer's patients. Florbetapir, like PiB, binds to beta-amyloid, but due to its use of fluorine-18 has a half-life of 110 minutes, in contrast to PiB's radioactive half life of 20 minutes. Wong et al. found that the longer life allowed the tracer to accumulate significantly more in the brains of the AD patients, particularly in the regions known to be associated with beta-amyloid deposits. Thus, in specific embodiment, a patient at risk is one that has increased Aβ deposits.

Volumetric MRI can detect changes in the size of brain regions. Measuring those regions that atrophy during the progress of Alzheimer's disease is showing promise as a diagnostic indicator. Thus, according to another specific embodiment, an at-risk patient is one that has an atrophic brain region.

Another recent objective marker of the disease is the analysis of cerebrospinal fluid for amyloid beta or tau proteins, both total tau protein and phosphorylated tau181P protein concentrations. Searching for these proteins using a spinal tap can predict the onset of Alzheimer's with a sensitivity of between 94% and 100%. Thus, according to another specific embodiment, a patient at risk is one that has elevated levels of tau and/or amyloid beta proteins in cerebral spinal fluid. When used in conjunction with existing neuroimaging, doctors can identify patients with significant memory loss who are already developing the disease.[31] Spinal fluid tests are commercially available, unlike the latest neuroimaging technology. Alzheimer's was diagnosed in one-third of the people who did not have any symptoms in a 2010 study, meaning that disease progression occurs well before symptoms occur. Changes in brain ventricle size may be measured by magnetic resonance imaging (MRI). This measurement provides, in another embodiment, the ability to diagnose pre-Alzheimer's disease or early stages of the disease in some cases. While neuro-cognitive assessments including the testing of memory, ability to problem solve, count, and other cognitive tests provides a diagnosis for Alzheimer's disease, a definitive diagnosis is not possible in the prior art until after death when an autopsy can be used to reveal the presence of amyloid plaques and tangles in brain tissue. Improvements have been made such that an earlier diagnosis may be made by identifying an increase in ventricle size in the brain associated with mild cognitive impairment in patients at risk for Alzheimer's disease or in the early stages of the disease. Therefore, according to a specific embodiment, a patient is at risk for a neurodegenerative disease, particularly AD, if the patient exhibits one or more of the foregoing factors or symptoms. In another specific embodiment, a patient at risk exhibits two or more of the aforementioned factors or symptoms.

In the case of Parkinson's disease (PD), a pattern of reduced dopaminergic activity in the basal ganglia can aid in diagnosis. Thus, in another specific embodiment, a patient at risk is one that has reduced dopaminergic activity in the basal ganglia. Also, Parkinson's disease affects movement, producing motor symptoms, such as Parkinsonian gait, tremors, rigidity, slowness of movement and postural instability. Non-motor symptoms, which include autonomic dysfunction, neuropsychiatric problems (mood, cognition, behavior or thought alterations), and sensory and sleep difficulties, are also common. Thus, according to another specific embodiment, a patient at risk is one that exhibits one or more motor or non-motor PD symptoms. In an even more specific embodiment, a patient at risk is one that has two or more of the foregoing factors or symptoms.

In a further aspect, a method of reducing brain inflammation in a subject is provided. The method includes administering a therapeutically effective amount of cerium oxide nanoparticles having a low 3+/4+ ratio to the subject, the cerium oxide nanoparticles effective to reduce nitrite oxide levels in the brain, thereby reducing peroxynitrite levels in the brain.

1.7 Pharmaceutical Compositions

Aspects of the present invention also provide pharmaceutical compositions comprising the cerium oxide nanoparticles described herein. The pharmaceutical compositions can be administered to a patient to achieve a desired therapeutic effect. The compositions can be administered alone or in combination with at least one other agent, such as a stabilizing compound, which can be administered in any sterile, biocompatible pharmaceutical carrier, including, but not limited to, saline, buffered saline, dextrose, and water. The compositions can be administered to a subject alone, or in combination with other therapeutic agents or treatments as described below.

In addition to the active ingredients, these pharmaceutical compositions can contain suitable pharmaceutically acceptable carriers comprising excipients and auxiliaries that facilitate processing of the active compounds into preparations which can be used pharmaceutically. Pharmaceutical compositions of the invention can be administered by any number of routes including, but not limited to, oral, intravenous, intramuscular, intra-arterial, intramedullary, intrathecal, intraventricular, transdermal, subcutaneous, intraperitoneal, intranasal, parenteral, topical, sublingual, or rectal means. Pharmaceutical compositions for oral administration can be formulated using pharmaceutically acceptable carriers well known in the art in dosages suitable for oral administration. Such carriers enable the pharmaceutical compositions to be formulated as tablets, pills, dragees, capsules, liquids, gels, syrups, slurries, suspensions, and the like, for ingestion by the subject.

Further details on techniques for formulation and administration can be found in the latest edition of REMINGTON'S PHARMACEUTICAL SCIENCES (Mack Publishing Co., Easton, Pa., which is incorporated herein by reference). After pharmaceutical compositions have been prepared, they can be placed in an appropriate container and labeled for treatment of an indicated condition. Such labeling would include amount, frequency, and method of administration.

1.8 Determination of a Therapeutically Effective Dose

The determination of a therapeutically effective dose for any one or more of the compounds described herein is within the capability of those skilled in the art. A therapeutically effective dose refers to that amount of active ingredient which provides the desired result. The exact dosage will be determined by the practitioner, in light of factors related to the subject that requires treatment. Dosage and administration are adjusted to provide sufficient levels of the active ingredient or to maintain the desired effect. Factors which can be taken into account include the severity of the disease state, general health of the subject, age, weight, and gender of the subject, diet, time and frequency of administration, drug combination(s), reaction sensitivities, and tolerance/response to therapy. Long-acting pharmaceutical compositions can be administered every 3 to 4 days, every week, or once every two weeks depending on the half-life and clearance rate of the particular formulation.

Normal dosage amounts can vary from 0.1 to 100,000 micrograms, up to a total dose of about 1 g, depending upon the route of administration. Guidance as to particular dosages and methods of delivery is provided in the literature and generally available to practitioners in the art. Preferably, a therapeutic agent gains access to the parasite or the infected red blood cell for the duration of time necessary for its normal action.

1.9 Conjunctive Therapeutic Agents

In any of the embodiments described above, any of the compounds and/or compositions of the invention can be co-administered with other appropriate therapeutic agents (conjunctive agent or conjunctive therapeutic agent) or therapies for the treatment or prevention of a disorder or condition associated with elevated nitric oxide levels and/or symptom(s) thereof. For example, the conjunctive agent may be any known therapeutic, treatment or therapy known for the treatment of a muscular disease, inflammatory bowel disease; sepsis; septic shock; primary headaches, an inflammatory disease, a cardiovascular-related condition; and/or a neurodegenerative disorder.

Selection of the appropriate conjunctive agents or therapies for use in combination therapy can be made by one of ordinary skill in the art, according to conventional pharmaceutical principles. The combination of therapeutic agents or therapies can act synergistically to effect the treatment or prevention of the diseases or a symptom thereof. Using this approach, one may be able to achieve therapeutic efficacy with lower dosages of each agent, thus reducing the potential for adverse side effects.

In certain embodiments, the conjunctive agent may include one or more additional nitric oxide scavengers, including but not limited to Carboxy-PTIO; DTCS; Hemoglobin, Bovine Erythrocytes; N-methyl-D-glucamine dithiocarbamate-$Fe^{2+}$ (MGD-Fe); and (+)-Rutin Hydrate.

In another embodiment, the conjunctive agent comprises a compound that is a scavenger of superoxide radical and/or peroxynitrite and/or a compound that inhibits the production thereof in vivo. For example, the conjunctive agent may comprise cerium oxide nanoparticles alternatively having a high 3+/4+ ratio, which will preferentially scavenge peroxynitrite.

In still another embodiment, the conjunctive may comprise a therapeutic agent or therapy effective in the treatment of any condition described herein associated with elevated levels of nitric oxide, superoxide or peroxynitrite.

The mode of administration for a conjunctive formulation in accordance with the present invention is not particularly limited, provided that the compounds of the present invention as described herein (low 3+/4+ ratio cerium oxide nanoparticles) and the conjunctive agent are combined upon administration. Such an administration mode may, for example, be (1) an administration of a single formulation obtained by formulating low 3+/4+ ratio cerium oxide nanoparticles and a conjunctive agent simultaneously; (2) a simultaneous administration via an identical route of the two agents obtained by formulating low 3+/4+ ratio cerium oxide nanoparticles and a conjunctive agent separately; (3) a sequential and intermittent administration via an identical route of the two agents obtained by formulating low 3+/4+ ratio cerium oxide nanoparticles and a conjunctive agent separately; (4) a simultaneous administration via different routes of two formulations obtained by formulating low 3+/4+ ratio cerium oxide nanoparticles and a conjunctive agent separately; and/or (5) a sequential and intermittent administration via different routes of two formulations obtained by formulating low 3+/4+ ratio cerium oxide nanoparticles and a conjunctive agent separately (for example, low 3+/4+ ratio cerium oxide nanoparticles followed by a conjunctive agent, or inverse order) and the like.

The dose of a conjunctive formulation may vary depending on the formulation of the low 3+/4+ ratio cerium oxide nanoparticles and/or the conjunctive agent, the subject's age, body weight, condition, and the dosage form as well as administration mode and duration. One skilled in the art would readily appreciate that the dose may vary depending on various factors as described above, and a less amount may sometimes be sufficient and an excessive amount should sometimes be required.

The conjunctive agent may be employed in any amount within the range causing no problematic side effects. The daily dose of a conjunctive agent is not limited particularly and may vary depending on the severity of the disease, the subject's age, sex, body weight and susceptibility as well as time and interval of the administration and the characteristics, preparation, type and active ingredient of the pharmaceutical formulation. An exemplary daily oral dose per kg body weight in a subject, e.g., a mammal, is about 0.001 to 2000 mg, preferably about 0.01 to 500 mg, more preferably about 0.1 to about 100 mg as medicaments, which is given usually in 1 to 4 portions.

When the low 3+/4+ ratio cerium oxide nanoparticles and a conjunctive agent are administered to a subject, the agents may be administered at the same time, but it is also possible that a conjunctive agent is first administered and then low 3+/4+ ratio cerium oxide nanoparticles are administered, or that low 3+/4+ ratio cerium oxide nanoparticles are first administered and then a conjunctive agent is administered. When such an intermittent administration is employed, the time interval may vary depending on the active ingredient administered, the dosage form and the administration mode, and for example, when a conjunctive agent is first administered, the low 3+/4+ ratio cerium oxide nanoparticles may be administered within 1 minute to 3 days, preferably 10 minutes to 1 day, more preferably 15 minutes to 1 hour after the administration of the conjunctive agent. When the low 3+/4+ ratio cerium oxide nanoparticles are first administered, for example, then a conjunctive agent may be administered within 1 minute to 1 day, preferably 10 minutes to 6 hours, more preferably 15 minutes to 1 hour after the administration of the low 3+/4+ ratio cerium oxide nanoparticles. It is also contemplated that more than one conjunctive agent may be administered to the subject if desired.

The following examples are provided as an aid in examining particular aspects of the invention, and represent only certain embodiments and explanations of embodiments. The examples are in no way meant to be limiting of the invention scope. The materials and methods provided below are those which were used in performing the examples that follow.

1.10 Nanoparticle Synthesis and Characterization

The cerium oxide nanoparticles were synthesized by wet chemical process as previously described.[22] Chemicals for $CeO_2$ nanoparticle synthesis, $Ce(NO_3)_3$, $H_2O_2$, were obtained from Sigma-Aldrich (St. Louis, Mo.). $SiO_2$ nanoparticles were purchased from Corpuscular Inc. (Cold Spring, N.Y.). The surface chemistry of the cerium oxide nanoparticles was studied using a Physical Electronics (5400 PHI ESCA) spectrometer with a monochromatic Al Kα X-ray source operated at 300 W and base pressure of $1\times10^{-9}$ Torr. The binding energy of the Au (4f7/2) at 84.0±0.1 eV was used to calibrate the binding energy scale of the spectrometer.

1.11 Assay for Nitric Oxide

A ferrous hemoglobin assay was adapted from Murphy & Noack[21] in which ferrous hemoglobin (Hb) (Sigma-Aldrich) and •NO react to form oxidized ferric hemoglobin. S-nitroso-N-acetylpenicillamine (SNAP) (Molecular Probes), was used to generate •NO. Briefly, 200 μM of SNAP was added to 25 mg/mL ferrous Hb in the presence or absence of nanoparticles or the spin-trap DEPMPO (Enzo Life Sciences) in 100 mM phosphate buffer (pH 7.0). The oxidation of Hb was monitored using a Hewlett-Packard 8453 diode array spectrophotometer. Changes to spectra at wavelengths of 411 nm (isosbestic point) and 421 nm were followed. The change in absorbance per unit time was measured for 10 min at 30 s intervals. The concentration of •NO reacting with Hb was obtained by the difference in absorbance between 401-421 nm using an extinction coefficient of 77 $mM^{-1}$ $cm^{-1}$.[21]

1.12 Surface Chemistry Alteration by Phosphate Icons

Phosphate buffer was prepared by dissolving monosodium phosphate (13.8 g/L) and its conjugate base, disodium phosphate (14.1 g/L), in 1 L of water to give a 0.1 M solution, and the pH was adjusted by titration with 1 M HCl to reach a pH value of 7.4. Water dispersed $CeO_2$ NPs with higher levels of oxygen vacancies at their surface (200 μM) were suspended in equimolar phosphate buffer (pH 7.4) for 24 h at room temperature. The UV-visible spectra were recorded to determine surface chemistry of cerium using a UV-viable Hewlett-Packard 8453 diode array spectrophotometer in a 1.0 cm path length quartz cuvette.

1.13 •NO Detection Using Copper-Fluorescein Method

To measure •NO by an alternate method, we followed •NO levels using a copper-fluorescein (Cu-FL) probe as previously described.[20] In these experiments, 100 μM of the •NO generator, diethylamine nonoate diethylammonium salt (DEA/NO) (Sigma) was added to CuFL probe (1 μM) (Strum Chemicals, Newburyport, Mass.). Fluorescence was followed at an emission wavelength of 530 nm using an excitation wavelength of 503 nm in 50 mM sodium phosphate buffer, pH 7.0, containing 20 μM DPTA using a Varian Cary Eclipse fluorescence spectrophotometer (Palo Alto, Calif.) for 20 min at room temperature. Assays were carried out in the presence or absence of $CeO_2$ NP, $SiO_2$ nanoparticles or glutathione (Fisher Scientific, Pittsburg, Pa.).

1.14 Transmission Electron Microscopy (TEM)

$CeO_2$ nanoparticle morphology was characterized using high-resolution transmission electron microscopy (HR-TEM). The $CeO_2$ nanoparticle preparations were deposited on carbon-coated copper grid (SPI supplies) for HRTEM analysis. HRTEM micrographs were obtained using FEI Tecnai F30 operated at 300 keV.

1.15 X-Ray Photoelectron Spectroscopy (XPS)

The $CeO_2$ nanoparticle were transferred onto silicon wafers (Kmbh Associates CZ Silicon, thickness of wafer: 350 μm) and air dried. The surface chemistry of the nanoparticles were studied using a Physical Electronics (5400 PHI ESCA) spectrometer with a monochromatic Kα X-ray source operated at 300 W and base pressure of $1\times10^{-9}$ Torr. The binding energy of the Au (4f7/2) at 84.0±0.1 eV was used to calibrate the binding energy scale of the spectrometer.

1.16 Zeta Potential (Zp) and Particle Size Measurement

Water dispersed $CeO_2$ NPs with different 3+/4+ ratios were suspended in buffers according to the various conditions used in these studies and ZP and particle size measured. For surface chemistry alteration experiments, NPs were incubated for 24 h followed by ZP and particle size measurements using Zeta sizer (Nano-ZS) from Malvern Instruments.

1.17 Results

To determine the reactivity of $CeO_2$ NPs with •NO under biologically relevant conditions, water-based $CEO_2$ NPs with different 3+/4+ ratios were synthesized and characterized as set forth in Table 1 below.

TABLE 1

Physiochemical properties of $CeO_2$ Nanoparticles

|  | 3+ | 4+ |
|---|---|---|
| Size (nm) | 5-8 | 3-8 |
| Zeta Potential - as synthesized ($H_2O$)(mV) | 15.1 | 49.2 |
| Zeta Potential - Hb assay buffer (mV) | −14.4 | −21.7 |
| Zeta Potential - CuFL assay buffer (mV) | −14.1 | −20.5 |
| XPS - Ce3+ (%) | 75 ± 3 | 20 ± 5 |

The reaction between •NO and the oxygenated, ferrous form of Hb can be used as a sensitive means to measure dissolved •NO. S-nitroso-N-acetylpenicillamine (SNAP) was used to generate •NO and we followed the conversion of the ferrous form of Hb to the ferric form of Hb by •NO.[12] Addition of $CeO_2$ nanoparticles with high 3+/4+ ratio (75% 3+) had no effect on •NO's ability to oxidize Hb suggesting no interaction with these nanoparticles. However, the addition of $CeO_2$ nanoparticles with low 3+/4+ ratio (20% 3+, Table 1) inhibited the ability of •NO to oxidize Hb in a dose dependent manner (FIG. 1B). This pattern was similar to that observed with the known •NO scavenger DEPMPO (FIG. 1B). This result suggests that $CeO_2$ NPs with low 3+/4+ ratio prevent •NO from oxidizing Hb.

Figure 4:
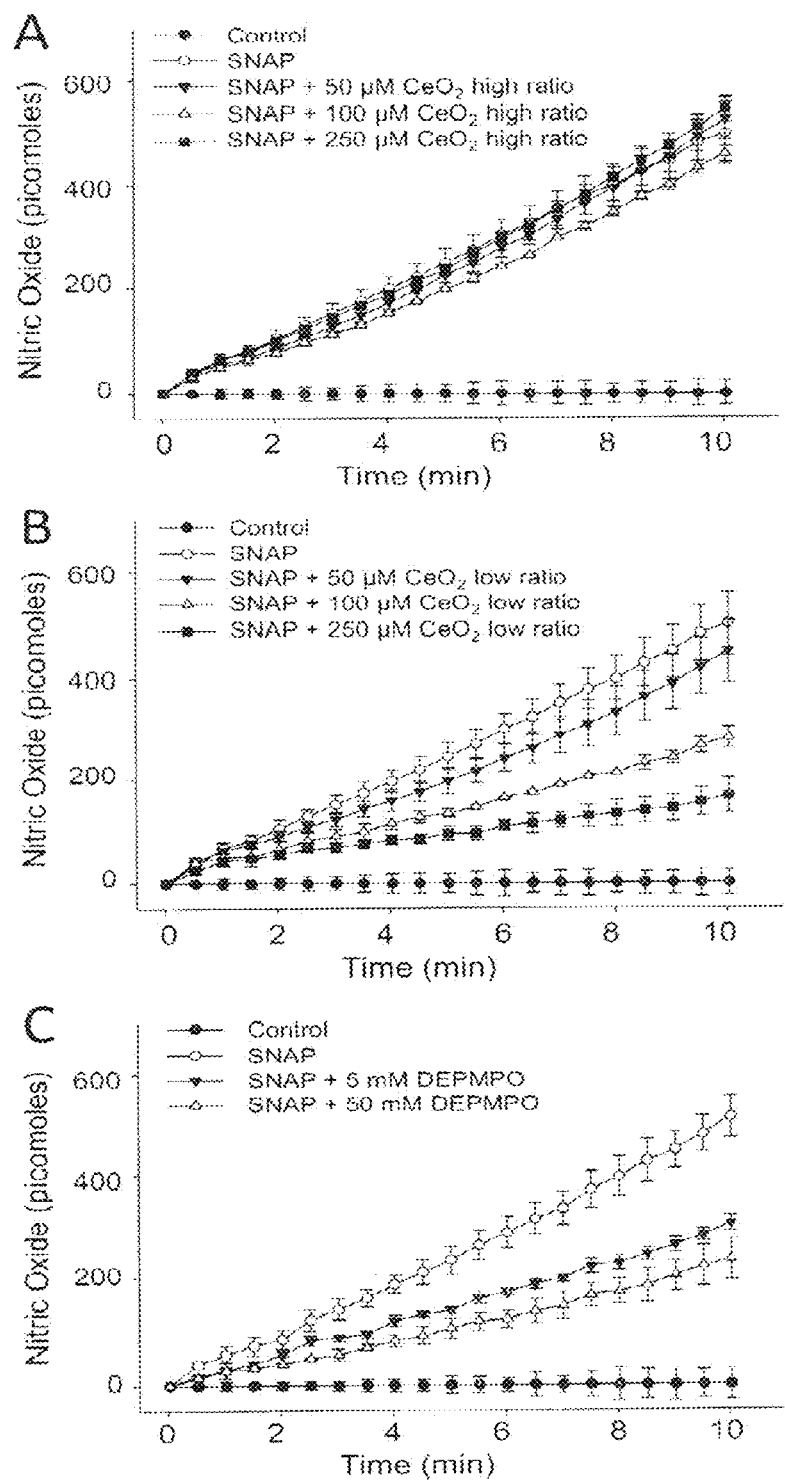
FIGS. 4A-C show the effective scavenging of •NO by $CeO_2$ nanoparticles lacking surface oxygen vacancies. The concentration of •NO in the presence or absence of $CeO_2$ nanoaparticles was quantified using the extinction coefficient for reaction with ferrous Hb (2). Data are derived from experimental data shown in FIG. 1. Represented in all graphs: closed circles=25 mg/mL Hb alone; open circles=25 mg/mL Hb+200 µM SNAP. A) $CeO_2$ NPs with high 3+/4+ ratio. B) $CeO_2$ NPs with low 3+/4+ ratio. C) DEPMPO addition. $CeO_2$ NPs or DEPMPO were added at the concentrations indicated. Graph is representative of 3 or more experiments.

To elucidate the scavenging efficiency of $CeO_2$ nanoparticles, we additionally determined the amount of dissolved •NO in the presence and absence of $CeO_2$ nanoparticles or DEPMPO translating the data obtained from Hb assay experiments. The concentration of •NO was obtained by difference in absorbance 401-421 nm using an extinction coefficient of 77 mM-1cm$^{-1}$[12] (FIG. 4). We observed concentration-dependent decreases in •NO in the presence of varying levels of Ce3+/Ce4+ ratio and were able to calculate the rates of radical formation in the presence or absence of the catalyst (Table 2 below).

TABLE 2

Changes in •NO levels in the presence of $CeO_2$ Nanoparticles

| Reaction Conditions | Nanoparticle(NP) concentration (μm) | NO Production Rate[a] (pmol $min^{-1}$ ± SD) |
|---|---|---|
| SNAP (200 μM) control | 0 | 51.6 ± 4.4 |
| SNAP + $CeO_2$ (flow 3+/4+) | 50 | 42.1 ± 5.7 |
|  | 100 | 25.8 ± 5.7 |
|  | 250 | 14.3 ± 3.3 |
|  | 250 | 52.5 ± 2.9 |
|  | 200 | 39.7 ± 5.9 |

[a]Rates are pmol$^{-1}$ and were calculated by determining the rate of change in absorbance per unit time, based on molar extinction coefficient of conversion of $HbO_2$ to metHb in the presence of •NO (401-421 nm)(Delta$^\epsilon$ = 77 $mM^{-1}$ $cm^{-1}$. SD = standard deviation.

Figure 2:
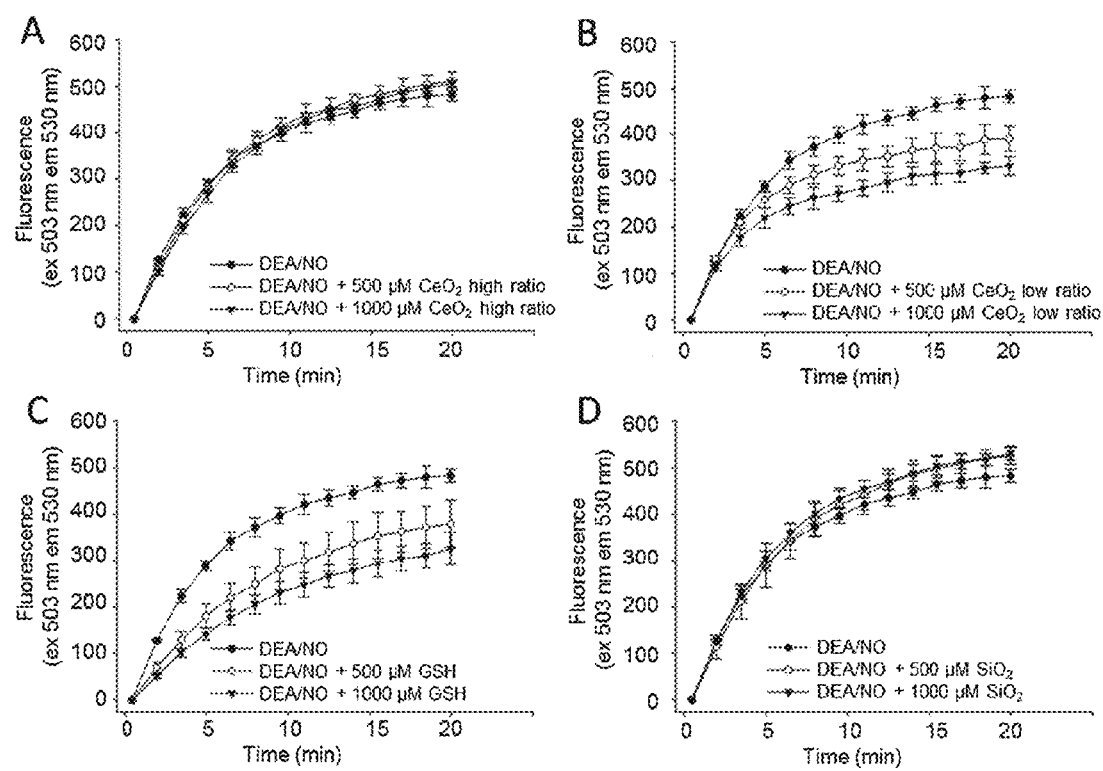
FIG. 2 confirms the scavenging of •NO by $CeO_2$ NPs using alternate fluorescence emission. Fluorescence emission was monitored at 530 nm upon excitation at 503 nm. Represented in all graphs; closed circles=100 µM DEA/NO. (A) $CeO_2$ NPs with high 3+/4+ ratio. (B) $CeO_2$ NPs with low 3+/4+ ratio. (C) GSH addition. (D) $SiO_2$ NPs addition. $CeO_2$ NPs, GSH or $SiO_2$ NPs were added at concentrations indicated. Graph is representative of 3 or more experiments.

In order to corroborate the data obtained from the Hb assay, we used an alternate detection method to determine $CeO_2$ nanoparticles ability to react with •NO. A derivatized copper fluorescein conjugate (Cu-FL) has been shown to be a specific detector of •NO production[13] though not as sensitive as Hb assay. Fluorescence emission at 530 nm was followed upon addition of 100 μM of the nonoate DEA/NO, another •NO donor, in the presence and absence of $CeO_2$ NPs. The addition of $CeO_2$ nanoparticles with high 3+/4+ ratio had no effect on the ability of dissolved •NO to oxidize the Cu-FL probe (FIG. 2A). When $CeO_2$ nanoparticles with low 3+/4+ ratio were included, we observed that the nanoparticles prevented the oxidation of the Cu-FL probe and that the fluorescent signal was decreased in a dose dependent manner (FIG. 2B). This reduction in fluorescent signal by $CeO_2$ nanoparticles with low 3+/4+ ratio is similar in efficacy as glutathione, a known •NO scavenger (FIG. 2C). By contrast, silicon oxide ($SiO_2$) control NPs of similar size, were unable to prevent the •NO-mediated Cu-FL oxidation (FIG. 2D) suggesting that the changes in dissolved •NO are specific to $CeO_2$ nanoparticles with low 3+/4+ ratio. Collectively, these data elucidate a previously unidentified catalytic property for $CeO_2$.

Figure 3:
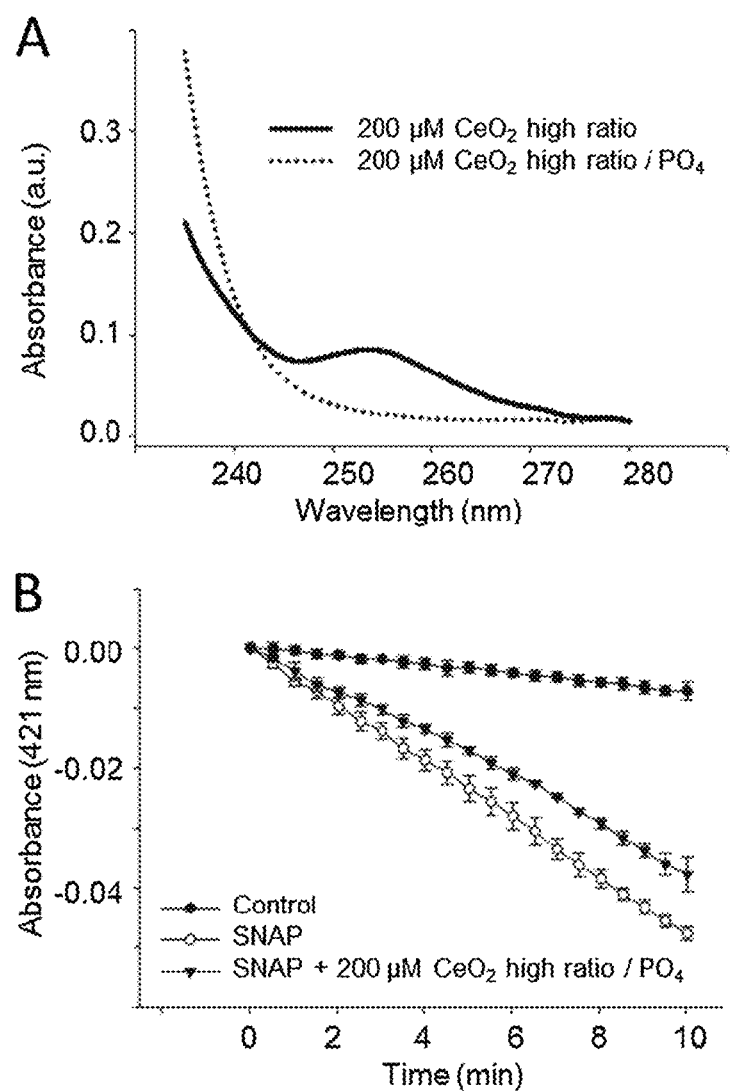
FIG. 3 shows $CeO_2$ NPs with a high level of surface oxygen vacancies can convert to •NO scavenging catalyst upon incubation with phosphate. (A) $CeO_2$ NPs were incubated in 200 mM sodium phosphate buffer at RT (room temp) for 24 h. Solid line represents $CeO_2$ NPs with higher levels of oxygen vacancies at their surface and dotted line represents sample incubated in phosphate. (B) •NO scavenging by $CeO_2$ NPs after incubation in phosphate. Closed circles=25 mg/mL Hb (Hemoglobin) alone; open circles=25 mg/mL Hb+200 µM SNAP; closed triangles=25 mg/mL Hb+200 µMSNAP+200 µM $CeO_2$ high Ce3+/$PO_4$. Graph is representative of 3 or more experiments.

Recently, it has been shown that incubation of $CeO_2$ nanoparticles with phosphate ions can interconvert these particles between the two catalyst (SOD or catalase mimetic) states.[14] To determine whether this property also applies to •NO scavenging, we incubated $CeO_2$ nanoparticles with phosphate and followed the presence of cerium atoms in the 3+ state (FIG. 3). The absorbance peak between 230-260 (consistent with $CeO_2$ nanoparticles with higher levels of oxygen vacancies) disappears after incubation with phosphate (FIG. 3A) as previously described.[14] After this conversion, $CeO_2$ nanoparticles are now able to effectively scavenge •NO (FIG. 3B and FIG. 5) indicating this surface chemistry 'switch' also correlates with •NO scavenging.

In summary, the above examples establish that the •NO scavenging capability of $CeO_2$ nanoparticles with low 3+/4+ ratio. •NO can be both electrophilic and nucleophilic in nature.[15] The nature of this heterogeneous catalysis is not yet fully understood. Yet one could envision a mechanism by which $CeO_2$ nanoparticles scavenge •NO through formation of an electropositive nitrosyl ligand due to internal electron transfer from •NO to a Ce4+ site:

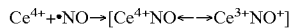

This mechanism has been found in various synthetic ferric porphyrin species[16] and manganese complexes.[17]

1.18 References

All references set forth herein in this document are incorporated by reference herein to the extent that the subject matter therein does not conflict with the existing disclosure.

1 A. B. Knott and E. Bossy-Wetzel, Antioxid. Redox Signaling, 2009, 11, 541-554.
2 E. Isenovic, S. Soskic, H. D. Dungen, B. Dobutovic, T. Elvis, I. Simone and P. Marche, Cardiovasc. Hematol. Disord. Drug Targets, 2011, 11, 669-702.
3 M. C. Martinez and R. Andriantsitohaina, Antioxid. Redox Signaling, 2009, 11, 669-702.
4 D. Pietraforte, A. M. Salzano, G. Marino and M. Minetti, Amino Acids, 2003, 25, 341-350.
5 T. Masui, T. Ozaki, K. Machida and G. Adachi, J. Alloys Compd., 2000, 303-304, 49-55.
6 Y. Y. Tsai, J. Oca-Cossio, S. M. Lin, K. Woan, P. C. Yu and W. Sigmund, Nanomedicine, 2008, 3, 637-645.
7 R. M. Ferrizz, T. Egami, G. S. Wong and J. M. Vohs, Surf. Sci., 2001, 476, 9-21.
8 M. Niwa, Y. Furukawa and Y. Murakami, J. Colloid Interface Sci., 1982, 86, 260-265.
9 G. S. Qi, R. T. Yang andR. Chang, Appl. Catal., B, 2004, 51, 93-106.
10 A. Martinez-Arias, J. Soria, J. C. Conesa, X. L. Seoane, A. Arcoya and R. Cataluna, J. Chem. Soc., Faraday Trans., 1995, 91, 1679.
11 M. A. Sharpe, R. Ollosson, V. C. Stewart and J. B. Clark, Biochem. J., 2002, 366, 97-107.
12 M. E. Murphy and E. Noack, Methods Enzymol., 1994, 233, 240-250.
13 M. H. Lim, D. Xu and S. J. Lippard, Nat. Chem. Biol., 2006, 2, 375-380.
14 S. Singh, T. Dosani, A. S. Karakoti, A. Kumar, S. Seal and W. T. Self, Biomaterials, 2011, 32, 6745-6753.
15 Nitric Oxide Biology and Pathobiology, ed. L. J. Ignarro, Academic Press, San Diego, 2000.
16 B. B. Wayland and L. W. Olson, J. Am. Chem. Soc., 1974, 96, 6037-6041.
17 M. R. Filipovic, K. Duerr, M. Mojovic, V. Simeunovic, R. Zimmermann, V. Niketic and I. Ivanovic-Burmazovic, Angew. Chem., Int. Ed., 2008, 47, 8735-8739.
18 A. Y. Estevez, S. Pritchard, K. Harper, J. W. Aston, A. Lynch, J. J. Lucky, J. S. Ludington, P. Chatani, W. P. Mosenthal, J. C. Leiter, S. Andreescu and J. S. Erlichman, Free Radical Biol. Med., 2011, 51, 1155-1163.
19 J. Niu, A. Azfer, L. M. Rogers, X. Wang and P. E. Kolattukudy, Cardiovasc. Res., 2007, 73, 549-559.
20. M. H. Lim, B. A. Wong, W. H. Pitcock, Jr., D. Mokshagundam, M. H. Baik, and S. J. Lippard. 2006. Direct nitric oxide detection in aqueous solution by copper(II) fluorescein complexes. J Am Chem Soc 128:14364-14373.
21. M. E. Murphy and E. Noack. 1994. Nitric oxide assay using hemoglobin method. Methods Enzymol 233:240-250.
22. S. Patil, S. C. Kuiry, S. Seal, and R. Vanfleet. 2002. Synthesis of nanocrystalline ceria particles for high temperature oxidation resistant coating. J Nanopart Res 4:433-438.
23. M. A. Ebrahimazadeh, S. F. Nabavi, S. M. Nabavi, F. Pourmorad,(2010). Nitric oxide radical scavenging potential of some Elburz medicinal plants. African J of Biotechnol. 9(32) 5212-5217.
24. G. Aliev, H. H. Palacios, A. E. Lipsitt, K. Fischbach, B. T. Lamb, M. E. Obrenovich, L. Morales, E. Gasimov, V. Bragin (2009). Nitric Oxide as an initiator of brain lesions during the development of Alzheimer disease. Neurotox. Res. 16: 293-305;
25. L. Zhang, V. L. Dawson , T. M. Dawson T M (2006). Role of nitric oxide in Parkinson's disease. Pharmacol. Ther. 109: 33-41.
26. A. K. Nath, J. A. Madri (2006). The roles of nitric oxide in murine cardiovascular development. Dev. Biol. 292: 25-33.
27. J. F. Parkinson, B. Mitrovic, J. E. Merrill. J Mol Med (Berl). The role of nitric oxide in multiple sclerosis. 1997 March; 75(3):174-86.
28. J. Dowling, T. Dosani, A. Kumar, S. Seal, W. T. Self (2012). Cerium oxide nanoparticles scavenge nitric oxide radical (•NO). Chem. Commun. 48: 4896-4898.
29. F. J. Bonte, T. S. Harris, L. S. Hynan, E. H. Bigio, C. L. White (July 2006). Tc-99m HMPAO SPECT in the differential diagnosis of the dementias with histopathologic confirmation. Clin Nucl Med 31 (7): 376-8.
30. N. J. Dougall, S. Bruggink, K. P. Ebmeier (2004). "Systematic review of the diagnostic accuracy of 99mTc-HMPAO-SPECT in dementia". Am J Geriatr Psychiatry 12 (6): 554-70.
31. G. De Meyer, F. Shapiro, H. Vanderstichele, E. Vanmechelen, S. Engelborghs, P. P. De Deyn, E. Coart, O. Hansson, L. Minthon, H. Zetterberg, K. Blennow, L. Shaw, J. Q. Trojanowski (August 2010). Diagnosis-Independent Alzheimer Disease Biomarker Signature in Cognitively Normal Elderly People. Arch Neurol. 67 (8): 949-56.
32. A. S., Karakoti, N. A., Monteiro-Riviere, R. Aggarwal, J. P. Davis, R. J. Narayan, W. T, Self, J. McGinnis, S. Seal (2008) Nanoceria as antioxidant: Synthesis and biomedical applications. JOM 60: 33-37.
33. R. Stuven, E. Bock, Wat. Res. Vol. 35, No. 8, pp. 1905-1914, 2001. Nitrification and Denitrification as a Source for NO and $NO_2$ Production in High Strength Wastewater.
34. M J, Kampschreur, C Picioreanu, N Tan, R, Kleerebezem, M S Jetten, M C van Loosdrecht. Water Environ Res. 2007 December; 79(13):2499-509. Unraveling the source of nitric oxide emission during nitrification.

It should be borne in mind that all patents, patent applications, patent publications, technical publications, scientific publications, and other references referenced herein and in the accompanying appendices are hereby incorporated by reference in this application to the extent not inconsistent with the teachings herein.

While various embodiments of the present invention have been shown and described herein, it will be obvious that such embodiments are provided by way of example only. Numerous variations, changes and substitutions may be made without departing from the invention herein. Accordingly, it is intended that the invention be limited only by the spirit and scope of the appended claims.

The invention claimed is:

1. A method for scavenging nitric oxide comprising contacting the nitric oxide with ceria nanoparticles comprising cerium in the 3+ and 4+ state and a low 3+/4+ ratio with decreased oxygen vacancies compared to ceria nanoparticles with a seventy-five (75) % 3+/4+ ratio, said ratios measured by x-ray photoelectron spectroscopy.

2. The method of claim 1, wherein the contacting is done within an exhaust stream from a combustion process.

3. The method of claim 1, wherein the contacting is done within a fluid stream following a wastewater treatment process.

4. The method of claim 1, wherein the contacting is done within a fluid following an etching or welding process.

5. The method of claim 1, wherein the low 3+/4+ ratio comprises 20±5% 3+ cerium oxide nanoparticles.

6. The method of claim 1, wherein the contacting is done in vivo.

* * * * *